United States Patent [19]
Horigane et al.

[11] Patent Number: 5,587,298
[45] Date of Patent: Dec. 24, 1996

[54] BIOREACTOR

[75] Inventors: Akira Horigane; Ushio Matsukura, both of Tsukuba; Masayoshi Kamio, Tsuchiura, all of Japan

[73] Assignee: Director General of National Agriculture Research Center, Ministry of Agriculture, Forestry and Fisheries, Ibaraki, Japan

[21] Appl. No.: 409,446

[22] Filed: Mar. 24, 1995

[30] Foreign Application Priority Data

Mar. 2, 1995 [JP] Japan ................................. 7-043316

[51] Int. Cl.$^6$ ............................. C12P 1/00; C12M 1/02
[52] U.S. Cl. .................... 435/41; 435/289.1; 422/135; 422/229; 366/300; 366/301
[58] Field of Search ............................. 435/41, 286.7, 435/289.1, 290.2, 293.1, 298.1, 306.1, 259; 422/135, 136, 137, 225, 229; 366/300, 301

[56] References Cited

U.S. PATENT DOCUMENTS

| 1,458,492 | 6/1923 | Mathews et al. | 366/300 |
| 2,686,336 | 8/1954 | Kleinlein et al. | 366/301 |
| 3,343,922 | 9/1967 | Zimmer et al. | 366/301 |
| 3,717,330 | 2/1973 | Pinney | 366/301 |
| 4,034,967 | 7/1977 | Gustairs | 366/301 |
| 4,277,585 | 7/1981 | Fournel et al. | 422/135 |
| 4,690,989 | 9/1987 | Kolinsky et al. | 422/135 |
| 5,108,711 | 4/1992 | Chszaniecki | 422/135 |

FOREIGN PATENT DOCUMENTS

| 2090808 | 4/1971 | France. | |
| 2638086 | 8/1976 | Germany. | |
| 8032619 | 2/1983 | Japan | 422/135 |
| 8368 | 2/1923 | Netherlands. | |
| 0768447 | 10/1980 | U.S.S.R. | 422/229 |
| 0778765 | 11/1980 | U.S.S.R. | 422/229 |
| 0803957 | 2/1981 | U.S.S.R. | 422/136 |

OTHER PUBLICATIONS

Database WPI, Section Ch, Week 9201, Derwent Publications Ltd., Class D15, AN 92–000234 & DD–A–292 437, 1 Aug. 1991, abstract.
Patent Abstracts of Japan, vol. 11, No. 124 (C–416), 17 Apr. 1987 & JP–A–61 264004, 21 Nov. 1986, abstract.
Patent Abstracts of Japan, vol. 12, No. 365 (C–532), 29 Sep. 1988 & JP–A–63 117038, 21 May 1988, abstract.

*Primary Examiner*—William Beisner
*Attorney, Agent, or Firm*—Flynn, Thiel, Boutell & Tanis, P.C.

[57] ABSTRACT

A bioreactor which and be used with substrates which are difficult to attain sufficient dispersion is made up of a reaction vessel 1 having a reaction chamber 2 surrounded by a water jacket 3 for maintaining a predetermined constant temperature. The reaction chamber 2 is provided in the vicinity of the inner wall surface 2a of the reaction vessel 2 with a plurality of upright screws 6 and 7 in an adjoining relationship to each other, each screw having a screw thread or a helical fin 6b, 7b of reverse turning sense with each other so that the reactor vessel contents are subjected to a convectional flow induced by the rotation of the screws in the reverse sense to each other by a gearing 14, 15. The substrate therein is subjected to a uniform agitation and to a milling and sieving actions in the portion 13 where the fins of the screws face each other, before the reaction product is removed by a screw conveyer 25.

9 Claims, 3 Drawing Sheets

BIOREACTOR

BACKGROUND OF THE INVENTION

The present invention relates to a bioreactor for performing biological and/or biochemical reactions. More specifically, the present invention relates to a bioreactor adapted for applying to quality assessment, analysis and so on, in systems difficult to attain, a uniform dispersion and mixing, such as those in the production of foods, biological samples and drugs etc.

Hitherto, three basic types of bioreactors have found their practical uses in realizing biological and biochemical reactions, namely, a stationary type, a shaking type and a rotating type. In conventional bioreactors, dynamic analyses of reactions have been attempted in general for diluted reaction systems using a low concentration substrate. However, few attempts have hitherto been successful at analyzing reaction systems with highly concentrated or insoluble substrates.

As a common stationary bioreactor, a fixedly settled reaction vessel, such as an Erlenmeyer flask, is employed in which a stirrer is arranged so as to realize a horizontal rotary movement to cause agitation of the reaction mixture, in order to increase the reaction rate. While this bioreactor permits an economical running of reaction, nevertheless, it cannot operate with a highly viscous substrate due to the shortage of driving torque of the stirrer. In this bioreactor, it is also a disadvantage that substrates with densities different from that of the solvent, i.e. the reaction medium, may tend to float up or sediment down to cause a separation of the reaction mixture.

In shaking type bioreactors, a shaking culture using test tubes as the culture vessel has widely been practised. In this system, the reaction is accelerated by reciprocating a horizontal movement of the culture vessel. This bioreactor can not serve for a highly viscous reaction system and, in addition, may encounter a problem of separation of the reaction mixture for a reaction system with a substrate having a density different from that of the reaction medium.

In rotating type bioreactors, those in which a reaction vessel, such as a test tube, with a plug closure is subjected to, for example, a circular motion by means of, for example, a rotator, to cause agitation of the reaction mixture, have found wide uses in practice. These bioreactors are suitable for reactions to be conducted with mild reaction rates, such as in a cell culture. Also in this type of bioreactors, however, the floating up of the substrate occurs for substrates having lower densities than that of the reaction medium and homogeneity may not be attained. In reaction systems evolving gases, the internal pressure will increase due to the tight plug closure, resulting in, occasionally, a leaking out of the reaction mixture. Since the bioreactors of this type are designed in general in a construction in which the reaction vessel, the mechanical driving arrangement and the control unit therefor are integrally combined, the entire installation should be accomodated in a constant temperature room. The employment of a constant temperature room brings about disadvantages in that a large investment is required and that it is accompanied by the occurrence of unstability of temperature upon openening and closure of the room door, since the thermostat therefor uses atmospheric air, which has a low specific heat, as the heat medium.

For improving such disadvantages of the prior techniques, a bioreactor was proposed (Japanese Patent Application Kokai No. 72957/1991), in which a planetary gear is incorporated within the reaction vessel for effecting milling and mixing of the reaction mixture, while imparting a convectional flow to the reaction mixture by a vertically arranged screw conveyer.

Upon operation of this bioreactor, however, the reaction mixture captured by the gear wheels is forced outside by the force generated upon rotation of the wheels, so that a simultaneous attainment of a uniform agitation and a milling effect is difficult for a reaction system with a high content of insoluble solid. Moreover, the construction of the apparatus is complicated. In addition, the milling action by the gear wheels may eventually cause damage to living microorganism.

SUMMARY OF THE INVENTION

An object of the present invention is to obviate the above-mentioned problems of the prior art and to provide a novel bioreactor for performing biological and/or biochemical reactions on substrates which may be present as insoluble solid matter exhibiting a tendency for floating up or sedimenting down in the reaction vessel or as a highly concentrated or highly viscous fluid and may be dispersed only difficultly, wherein the bioreactor enables the milling and dispersing of the substrate to mix it uniformly, while effecting exhaustion of the spent substrate under separation by, for example, sieving, to thereby attain a continuous operation of the bioreactor under preservation of the invariability of the reaction condition in the vessel for a long period of time.

According to the present invention, a novel bioreactor for realizing biological and/or biochemical reactions on substrates in the presence of microorganism(s) or chemical substance(s) is provided, which comprises a reaction vessel for carrying out the reaction therein, a plurality of screws arranged in the reaction vessel substantially vertically, in parallel and in an adjoining relationship to each other for guiding the contents of the reaction vessel in vertical direction by capturing it by two adjoining rotating screws between the confronting screw threads, a temperature conserving device for maintaining the reaction vessel at a predetermined temperature, a device for supplying the reaction vessel with the substrate and a device for removing the reaction mixture from the reaction vessel.

According to the present invention, also a method for realizing biological and/or biochemical reactions in the presence of microorganism(s) or chemical substance(s) is provided, which comprises introducing a substrate into a reaction vessel of a bioreactor equipped with a plurality of vertically disposed parallel screws for guiding the reaction mixture in the vessel in a vertical direction, conducting the reaction under the operation of the bioreactor so as to rotate the screws to cause of the reaction mixture to move in a vertical direction to effect a series of works of dispersing, mixing, milling and sieving off of the substrate.

DETAILED DESCRIPTION OF THE INVENTION

Figure 1:
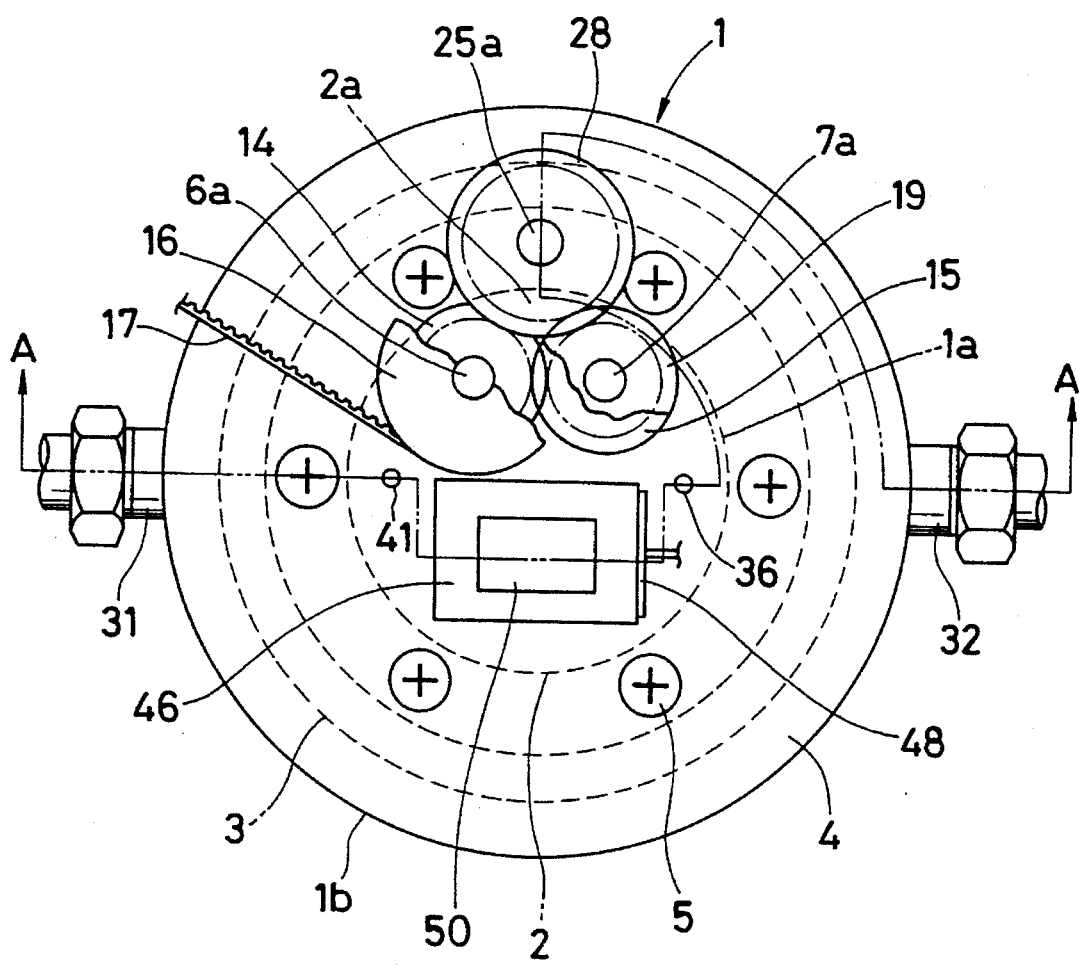
FIG. 1 is a plan view showing one embodiment of the bioreactor according to the present invention.

In the bioreactor according to the present invention, the reaction vessel and components contacting with the reaction mixture may preferably be made of a material which is inert to the reaction mixture in both biological and chemical natures without exhibiting any toxicity to the microorganism and any catalytic poison to the reaction, such as a polytetrafluoroethylene resin or an acrylic resin.

Any design may be applied to the screws, so long as a plurality of screws are arranged substantially in parallel and in an adjoining relationship to each other in such a manner that the contents of the reaction vessel is captured by two adjoining rotating screws between the confronting screw threads and is guided in the vertical direction in the reaction vessel. However, it is preferable that the two parallel screws each have a successive helical screw thread or fin turning in the opposing sense to each other and confronting each other and are disposed to permit their rotation in the reverse sense to each other, wherein it is especially preferable that the two screws each have a pitch nearly the same with each other. Here, the screws may be made of a material which is inert to the reaction environment and coupled together with rough-pitched screw threads or fins of a reverse turning sense with respect to each other, wherein the two screws are connected to a gearing disposed in an upper portion of the reaction vessel and are driven in a motion-coupled relation to effect rotation of these screws in the reverse sense with respect to each other, to thereby cause the reaction vessel contents to be guided in a vertical direction either upwards or downwards to reach an efficient agitation of the reaction mixture.

For driving the screws, it is preferable to use a driving unit composed of a driving motor and a transmission mechanism for transmitting the driving power to the screws in reverse rotational sense through the gearing disposed above them.

When the plurality of screws are arranged in the reaction vessel close to the inner wall surface of the reaction vessel and a device for removing the reaction mixture is arranged at a position at which the reaction mixture is liberated from the screws, a sieved reaction product can be taken out of the bioreactor. For the device for removing the reaction mixture, a screw conveyer may be adopted, but the use of other pertinent apparatuses may of course be permitted.

For the temperature controlling device for maintaining the reaction vessel at a predetermined temperature, an arrangement with a water jacket surrounding the reaction vessel through which water at a constant temperature is circulated from a constant temperature bath may be preferable.

For the device for supplying the reaction vessel with a substrate, it may be chosen in accordance with the mode of the reaction, while it is possible to employ such an embodiment in which the substrate is supplied from, for example, a hopper at a constant rate by dosing a predetermined amount of the substrate in each time interval.

It is preferable to control the operation of the driving unit for the screws, the temperature controlling device, the substrate supplying device and the reaction product removing device using a control unit including a computer.

For conducting a biological or biochemical reaction using the bioreactor according to the present invention, the reaction vessel is supplied with a substrate while maintaining the reaction vessel at a predetermined temperature by operating the temperature controlling device and the reaction is carried out on the substrate in the presence of one or more microorganisms or one or more chemical substances, such as enzymes, under actuation of the driving unit for the screws. By the rotation of these screws, the contents of the reaction vessel are guided vertically in the reaction vessel either upwards or downwards while being milled and sieved, to effect dispersion and mixing of the substrate. By selecting a smaller distance between the adjoining screws, the reaction mixture captured between the confronting screw theads or the helical fins will compressedly be forced towards the advancement of the rotating screws, whereby the solid particles of the substrate will be subjected to an action of attrition with each other and are thus milled mechanically.

When the screws are arranged close to the reaction vessel inner wall surface, a squeezing action is imparted to the reaction mixture on the side of the inner wall surface of the reaction vessel to thereby cause the smaller size particles formed by the milling action to come together, whereby a sieving of the solid particles are attained.

The reaction vessel contents guided in the vertical direction are then deflected at the upper or lower portion of the vessel laterally and cause a convectional flow, whereby the substrate particles are dispersed and mixed uniformly. In this manner, reactions can be realized under a condition in which the substrate is dispersed and mixed uniformly, even if a uniform dispersion of the substrate is attainable only difficultly, such as in the case where the substrate is present as insoluble solid particles and tends to float up or sediment down in the reaction medium or in the case where it appears as a highly concentrated or highly viscous fluid. A part of the reaction mixture is removed from the reaction vessel through the device for removing the reaction mixture.

The reaction can be conducted in accordance with a specific program set in the computer of the control unit and it is possible to conduct the reaction under a predetermined condition continuously for a long period of time. By controlling the agitation condition in the reaction vessel, it is possible to employ a mild agitation, whereby a reaction conducted while maintaining a feeble microorganism, such as a protozoa, may be realized.

In the reactions, substrates having a floating or sedimenting nature may effectively be dispersed in the reaction medium, e.g. a culture medium, by an agitating effect due to the convectional flow and by the milling effect due to the compressive attrition of the particles. When the substrate is present as insoluble solid particles, a mechanical milling of the substrate can be attained and the reaction can be conducted without incorporating a special pretreatment, such as an esterification for a substrate of low density oil or fat.

If the reaction vessel is designed in a construction which permits the maintenance of a gas-tight condition, a voluntary gas, such as an anaerobic gas, can be chosen to thereby enable the carrying out a culture of, for example, an obligate anaerobic microorganism, easily.

As described above, according to the bioreactor of the present invention, the substrate can effectively be milled to reach a uniform dispersion and mixing in the reaction medium and the reaction product can be withdrawn from the reaction vessel under separation by sieving, under a condition in which the substrate is dispersed and mixed uniformly, even if a uniform dispersion of the substrate is attainable only difficultly, such as in the case where the substrate is present as insoluble solid particles and tends to float up or sediment down in the reaction medium or in the case where it appears as a highly concentrated or highly viscous fluid, whereby a continuous operation of the bioreactor can be achieved under the preservation of the invariability of the reaction conditions in the vessel for a long period of time.

PREFERRED EMBODIMENT OF THE INVENTION

Below, the present invention is described by way of a preferred embodiment with reference to the appended Drawings. This embodiment illustrates a bioreactor adapted for a biological or biochemical reaction using a powder of cereal seeds (sesame, rice or the like) as the substrate.

Figure 2:
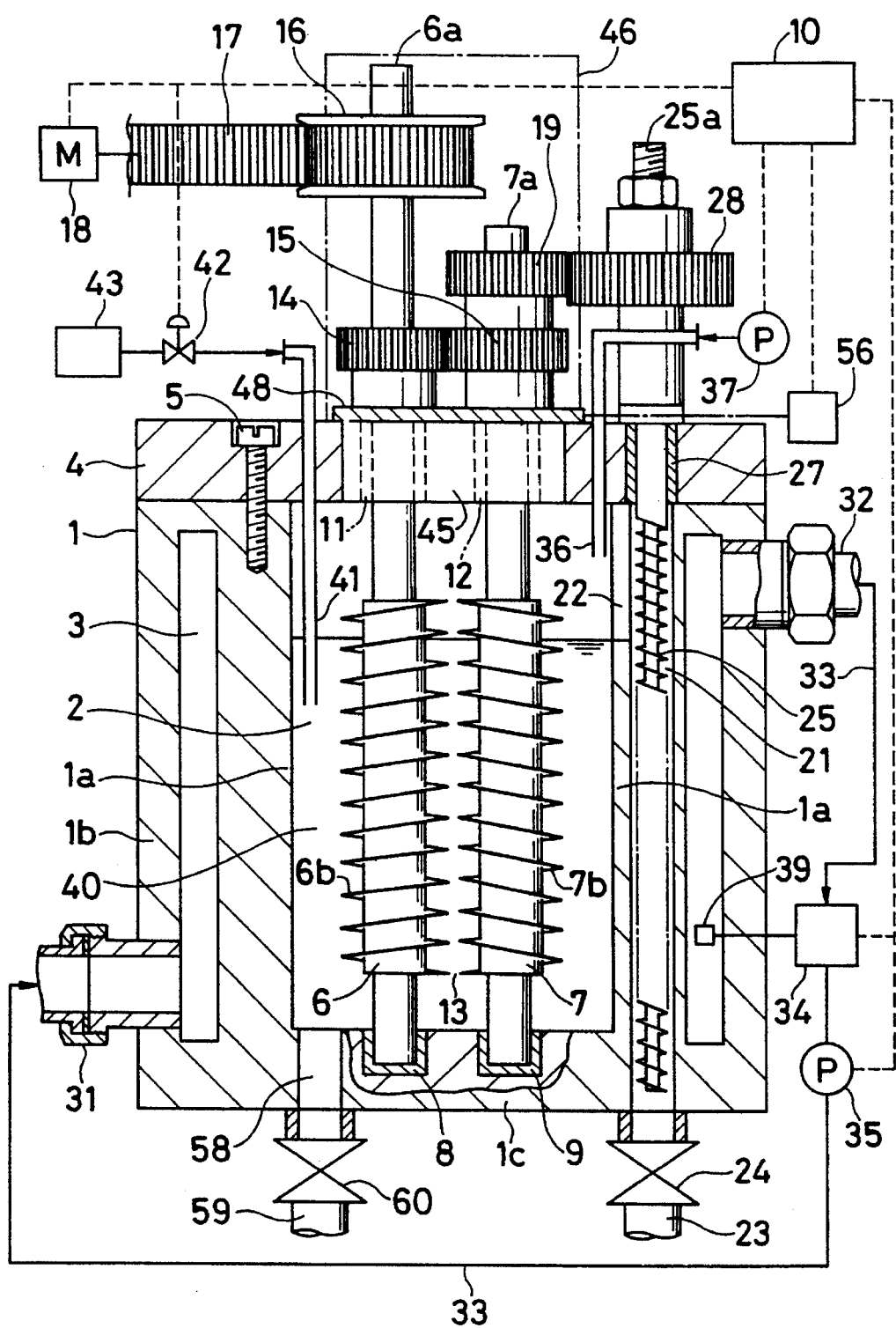
FIG. 2 shows the bioreactor in a sectional view along the line A—A of FIG. 1 under omission of the substrate supplying device.
Figure 3:
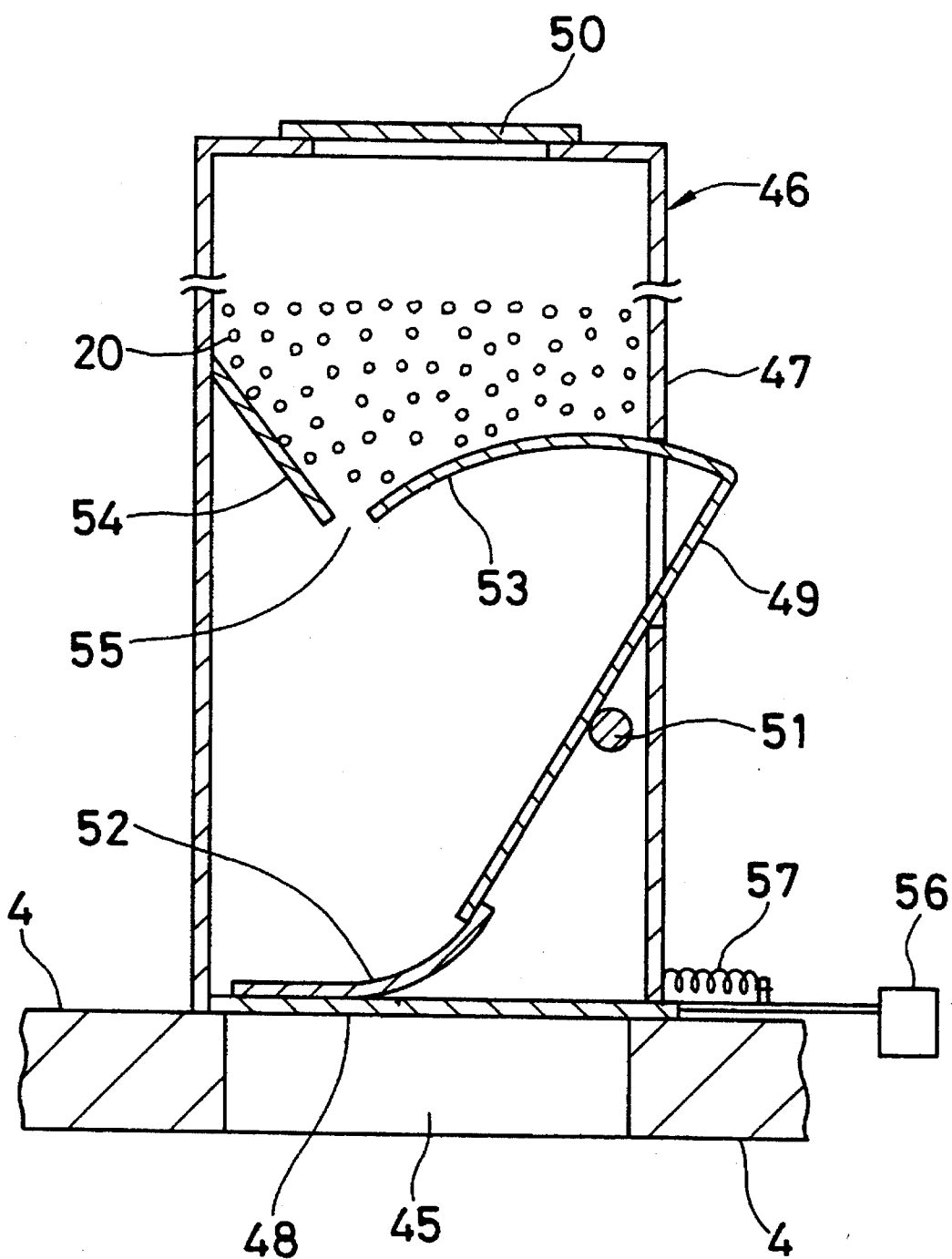
FIG. 3 shows the substrate supplying device of the bioreactor in a sectional view along the line A—A of FIG. 1.

FIG. 1 is a plan view of the bioreactor, FIG. 2 is a sectional view thereof along the line A—A with its hopper being neglected and FIG. 3 shows the hopper in the section along the line A—A, wherein the plane of section is locally changed as indicated in FIG. 1 to help understanding.

In FIGS. 1 and 2, the numeral 1 denotes the reaction vessel having a cylindrical reaction chamber 2 surrounded by a double wall consisting of an inner wall 1a and an outer wall 1b defining therebetween a water jacket 3. The reaction vessel 1 is tightly closed by a lid 4 fixed thereon by screw bolts 5. The reaction vessel 1 and the lid 4 are made of an inert material, such as an acrylic resin, and are arranged in a gas-tight construction. Closely adjacent to the inner wall surface 2a of the reaction chamber 2, there are arranged two screws 6 and 7 in an upright posture, of which shafts 6a and 7a are rotatably supported at their lower ends in bearing elements 8 and 9 on the bottom wall 1c of the vessel and at their upper portions in bearing elements 11 and 12, respectively, and project out through the lid 4. The screws 6 and 7 are arranged in a closely adjoining relation to each other and have each a helical fin 6b or 7b each having the same rough-pitch but in the opposing turning sense to each other. The two screws are disposed so that their helical fins align top-to-top to each other at the nearest confronting portion 13 of the screws. The screws 6 and 7 are made of an inert material, such as polyacetal resin.

The shafts 6a and 7a of the screws 6 and 7 are provided each at the portion projecting above the lid 4 with a toothed wheel 14 or 15, respectively, held in engagement with each other. The shaft 6a is further provided above the toothed wheel 14 with a timing wheel 16 used for the transmission of the driving power from a pulse motor 18 via a timing belt 17. The shaft 7a is further provided above the toothed wheel 15 with another toothed wheel 19.

Within the inner wall 1a at a position in front of the nearest confronting portion 13 of the screws 6 and 7 a vertically extending removed path 21 for removing the reaction product is provided which communicates at its upper part with the reaction chamber 2 through a communicating opening 22 and at its lower part to a removal line 23 via a valve 24. The removal path 21 is provided therein with a screw conveyer 25 of which shaft 25a is rotatably supported at its upper portion in a bearing element 27 in the lid 4. The shaft 25a is provided at the portion projecting above the lid 4 with a toothed wheel 28 which is held in engagement with the toothed wheel 19.

At a lower portion of the outer wall 1b, an inlet 31 for a constant temperature water to the water jacket 3 and, at an upper portion on the opposite side thereof, an exit 32 for the water jacket 3 is disposed, respectively, both of which are connected to a constant temperature bath 34 via a circulation line 33 and a circulation pump 35. The constant temperature bath 34 is controlled so as to maintain a constant temperature by the temperature signals from a heat sensor 39. A culture solution supply line 36 opens into the reaction chamber 2 through the lid 4 to permit supply of the culture solution by a feed pump 37. Also a gas supply line 41 connected to a gas bomb 43 via a control valve 42 opens into the reaction chamber 2 to permit supply of the gas to the reaction mixture 40 in the chamber through the lid 4.

A substrate supply inlet 45 is disposed near the center of the lid 4, above which a substrate supply unit 46 is arranged. As shown in FIG. 3, the substrate supply unit 46 is provided with a shutter plate 48 at the bottom of its casing 47 and with a swinging type weighing device 49 arranged to permit swinging around the axis 51 at its upper portion. The lower portion of the weighing device 49 is connected with the shutter plate 48 by a flexible connection member 52. Above the weighing device 49 is formed a movable arcuate hopper part 53 so as to operate the of opening and closure of the passage 55 between it and a fixed hopper part 54. The shutter plate 48 opens and closes the supply unit by actuating a solenoid 56 to retract the shutter plate and by deactivating it to restore it to the closed position by a compression spring 57. 50 represents an inlet for replenishing the substrate.

As seen in FIG. 2, the reaction vessel 1 is provided in its bottom 1c with an exhaustion path 58 communicating with an exhaustion line 59 via a valve 60. 10 denotes a control unit including a computer, an input unit, an output unit etc., which is connected electrically for controlling the pulse motor 18, the constant temperature bath 34, the circulation pump 35, the feed pump 37, the control valve 42, the solenoid 56 and so on.

A biological or biochemical reaction using the bioreactor described above is performed in the following manner: The constant temperature bath 34 is first adjusted to a predetermined temperature by a command from the control unit 10, whereupon water having the so-adjusted constant temperature is allowed to enter into the water jacket 3 by actuating the circulation pump 35 through the circulation line 33 and the water inlet 31 and is caused to circulate through them to maintain the temperature of the inside of the reaction chamber 2 at the corresponding constant temperature. Then, the culture solution (a buffer, a liquid culture medium or the like) is supplied to the reaction chamber 2 by actuating the feed pump 37 by a command signal from the control unit 10. In a similar manner, the control valve 42 is actuated to supply the reaction chamber 2 with a gas (such as $N_2$, $CO_2$ or the like) from the gas bomb 43 via the gas supply line 41.

On the other hand, the substrate supplying device 46 is operated by actuating the solenoid 56 at a predetermined time interval by a command signal from the control unit 10 to cause the shutter plate 48 to open and the weighing device 49 to swing open to effect dosage of the substrate, whereby the reaction chamber 2 is supplied with the substrate through the substrate supply inlet 45. Here, the weighing device 49 operates to close the passage 55 by swinging the movable part around the axis 51 to effect the weighing of one dosage of the substrate 20, which is supplied to the reaction chamber 2 through the supply inlet 45, whereupon the shutter plate 48 returns to the original position by the compression force of the spring 57, whereby the passage 55 opens again to allow the substrate 20 to fall down on the shutter plate 48.

In the state described above, the pulse motor 18 is actuated by a command signal from the control unit 10 to cause the screws 6 and 7 to rotate and the reaction is conducted in the presence of one or more microorganisms or one or more chemical substances such as enzymes. Here, the torque of the pulse motor 18 is transmitted to the timing wheel 16 via the timing belt 17, wherein the torque is further transmitted to the shaft 7a by the toothed wheels 14 and 15 upon rotation of the shaft 6a. By this, the screws 6 and 7 are caused to rotate in an opposing sense to each other, so that the reaction mixture existing around them are guided in a vertical direction, either upwards or downwards.

The reaction mixture 40 existing between the opposing helical fins 6b and 7b at the confronting portion 13 of the two screws 6 and 7 is subjected to a compressive transportational action due to the narrow space restricted by the screws 6 and 7 as well as due to the restriction of vertical movement of the reaction mixture by the presence of the fins, whereby a milling of the particles occurs due to an attritional effect between the particles with each other, resulting in a reduction of the particle size. Within the space surrounded by the screws and the inner wall surface 1a on the side of the communicating opening 22, a lifting flow path 2a is built up. In this area, small sized particles formed by the milling and passed through the confronting portion 13 come together, whereby a sieving action occurs. All the reaction mixture portions lifted around the screws 6 and 7, including that in the lifting flow path 2a, are deflected into a horizontal flow at the upper end to thereby cause formation of a convectional flow so that the reaction mixture containing the substrate will be homogenized.

Even if the substrate is insoluble and tends to sediment down and is present in a high concentration, a uniform mixing thereof is attained by the rotation of the screws 6 and 7. If the substrate tends to float up, it can be forced to flow down by rotating the screws in the reverse direction.

Upon rotating the shaft 7a, the screw conveyer 25 is rotated by the rotation of the toothed wheels 19 and 28. Thus, a sieving action occurs by the rotation of the screws 6 and 7, whereby small-sized particles will come together in the lifting flow path 2a and a part of the reaction product brought up in the lifting flow path 2a enters the removal path 21 from the communicating opening 22 and is forced to flow down and removal from the removal line 23 by the rotation of the screw conveyer 25. The amount to be removal from the path 21 is adjusted by the revolution rate of the screw conveyer 25 and the degree of opening of the valve 24. The exhaustion line 59 and the valve 60 exhaust the entire reaction mixture when the operation of the bioreactor is stopped.

The above-described bioreactor permits a voluntary selection of the revolution rate of the screws in the range from a mild rotation to a high speed rotation, by controlling the number of pulses supplied to the pulse motor 18, wherein it is possible, therefore, to generate a large torque in a low speed operation for avoiding damage to the microorganism or the enzyme to promote the reaction. By the convective flow produced by the screws 6 and 7, the substrate can effectively be dispersed in the culture medium regardless of the specific weight value by the convectional action caused by the screws 6 and 7 and the internal mixing of the reaction mixture can efficiently be attained even for a highly viscous substance due to the permissible high torque.

In this manner, the bioreactor according to the present invention can afford to attain an effective dispersion of substrates which tend to float up or sediment down in the reaction mixture within the reaction vessel 2, whereby maintenance of the uniformity of the reaction mixture can be realized by effecting agitation in the reaction vessel with a sufficient torque, even in a highly viscous condition. By keeping the reaction vessel in a gas-tight condition, special gas phase systems, such as those to be incorporated in an aerobic or in an anaerobic reaction, can be selected for the reaction system. Due to the permission of a computer control of the condition of agitation of the reaction mixture, a wide range of reactions such as from a cell culture requiring a mild agitation to a biochemical reaction requiring vigorous agitation can be dealt with voluntarily with better reproducibility. Even with a substrate of an insoluble solid, there is no need for converting the substrate into a soluble derivative since the bioreactor according to the present invention provides a mechanical milling of the substrate with the screws 6 and 7.

As an experimental example, a biological reaction was carried out, in the presence of microorganisms existing in the ruminant stomach of a sheep under an anaerobic condition at 39° C. using unmilled rice grains as a substrate having a high specific gravity, on the one hand, and using sesame seeds as a substrate having a low specific gravity, on the other hand.

In the case of the rice grains, the screws 6 and 7 were rotated so as to cause an upward flow of the reaction mixture and, for the case of sesame seeds, the screws 6 and 7 were rotated reversely, to carry out the biologcal reaction. In both the cases, the substrate was dispersed in the bioreactor and was taken up by the microorganisms. In the case of sesame seeds, the reaction product was removal downwards from the reaction vessel by using a reversing screw for the screw conveyer 25.

In an ordinary shaking biological reaction using test tubes, both the rice grains and the sesame seeds were scarcely dispersed in the test tube and the rate of intake by the protozoa was low.

While the above Example deals with the biological reaction of microorganisms with a substrate, the bioreactor according to the present invention can be applied to other biological and biochemical reactions with high substrate concentrations, such as fermentation, waste water treatment and organic and inorganic biochemical reactions.

We claim:

1. A bioreactor for performing biological and biochemical reactions involving a substrate, a microorganism or a chemical substance, said bioreactor comprising:

a reaction vessel for carrying out a reaction therein;

a plurality of screws contained in said reaction vessel, said screws being provided in parallel relationship with a vertical axis of said reaction vessel and adjacent to an inner wall surface of the reaction vessel so that a vertical flow path for a reaction product is formed between the inner wall surface and the screws, each of said screws having a screw thread provided therearound with a threading sense opposite to that of an adjacent screw;

means for rotating adjacent screws in a direction opposite to each other so that a reaction mixture provided in said reaction vessel is pumped in a vertical direction and causes a mixing of the reaction mixture and a milling of particles contained in the reaction mixture by attrition between the particles and forms a sieving action by passing small particles into the vertical flow path through opposing surfaces of adjacent screws;

a temperature controlling device for maintaining the reaction vessel at a predetermined temperature;

means for supplying the reaction vessel with at least one substrate; and means for removing the reaction product from the vertical flow path.

2. A bioreactor as claimed in claim 1, wherein the means for removing the reaction product is provided at a location in the reaction vessel at which the reaction product is liberated from the screw conveyors.

3. A bioreactor as claimed in claim 1, wherein the means for removing the reaction product is a screw.

4. A bioreactor as claimed in claim 1, additionally comprising a gas bomb for supplying a gas to the reaction vessel.

5. A method for performing biological and biochemical reactions involving a substrate, a microorganism or a chemical substance, said method comprising the steps of:

introducing at least one substrate into a reaction vessel of a bioreactor containing at least one member selected from the group consisting of one or more microorganisms and one or more chemical substances, said reaction vessel having a plurality of screws provided therein in a parallel relationship with a vertical axis of said reaction vessel and adjacent to an inner wall surface of the reaction vessel so that a vertical flow path for a reaction product is formed between the inner wall surface and the screws, each of said screws having a screw thread provided therearound with a threading sense opposite to that of an adjacent screw;

conducting at least one reaction in the bioreactor such that adjacent screws rotate in a direction opposite to each other so that a reaction mixture provided in said reaction vessel is pumped in a vertical direction and causes a mixing of the reaction mixture and a milling of particles contained in the reaction mixture by attrition between the particles and forms a sieving action by passing small particles into the vertical flow path through opposing surfaces of adjacent screws; and removing the reaction product from the vertical flow path.

6. The method of claim 5, wherein said substrate is cereal seed powder.

7. The method of claim 5, wherein a microorganism is present in said reaction mixture.

8. The method of claim 7, wherein said substrate is a mixture of unmilled rice grains and sesame seeds.

9. The method of claim 7, wherein said reaction is conducted under anaerobic conditions.

* * * * *